(12) United States Patent
Mansfield et al.

(10) Patent No.: US 7,227,925 B1
(45) Date of Patent: Jun. 5, 2007

(54) GANTRY MOUNTED STEREOSCOPIC IMAGING SYSTEM

(75) Inventors: Stan Mansfield, Sunnyvale, CA (US); Marcel Marc, San Jose, CA (US)

(73) Assignee: Varian Medical Systems Technologies, Inc., Palo Alto, CA (US)

( * ) Notice: Subject to any disclaimer, the term of this patent is extended or adjusted under 35 U.S.C. 154(b) by 0 days.

(21) Appl. No.: 10/264,111

(22) Filed: Oct. 2, 2002

(51) Int. Cl.
*A61N 5/10* (2006.01)
(52) U.S. Cl. .......................... 378/65; 378/41; 600/427
(58) Field of Classification Search .................. 378/65, 378/41, 64, 193, 197; 600/427
See application file for complete search history.

(56) References Cited

U.S. PATENT DOCUMENTS

| | | | |
|---|---|---|---|
| 3,133,227 A | 5/1964 | Brown et al. .............. 315/5.42 |
| 3,144,552 A | 8/1964 | Schonberg ................. 250/400 |
| 3,193,717 A | 7/1965 | Nunan ........................ 313/426 |
| 4,149,247 A | 4/1979 | Pavkovich et al. |
| 4,149,248 A | 4/1979 | Pavkovich et al. |
| 4,208,675 A | 6/1980 | Bajon et al. .................. 348/94 |
| 4,209,706 A | 6/1980 | Nunan ........................ 378/189 |
| 4,521,808 A | 6/1985 | Ong et al. .................... 378/29 |
| 4,593,967 A | 6/1986 | Haugen ........................ 359/18 |
| 4,675,731 A | 6/1987 | Takasu et al. .............. 378/98.3 |
| 4,679,076 A | 7/1987 | Vikterlof et al. ............ 348/142 |
| 4,726,046 A | 2/1988 | Nunan ........................ 378/65 |
| 4,741,621 A | 5/1988 | Taft et al. .................... 356/606 |
| 4,825,393 A | 4/1989 | Nishiya ....................... 702/152 |
| 4,853,777 A | 8/1989 | Hupp .......................... 348/128 |
| 4,868,844 A | 9/1989 | Nunan ......................... 378/152 |
| 5,008,907 A | 4/1991 | Norman et al. ............... 378/65 |
| 5,027,818 A | 7/1991 | Bova et al. .................. 600/427 |
| 5,080,100 A | 1/1992 | Trotel ......................... 600/407 |
| 5,099,505 A | 3/1992 | Seppi et al. |
| 5,117,445 A | 5/1992 | Seppi et al. |
| 5,168,532 A | 12/1992 | Seppi et al. |
| 5,207,223 A | 5/1993 | Adler .......................... 600/427 |
| 5,233,990 A * | 8/1993 | Barnea ........................ 600/427 |
| 5,335,255 A | 8/1994 | Seppi et al. |
| 5,394,452 A | 2/1995 | Swerdloff et al. ............. 378/65 |
| 5,427,097 A | 6/1995 | Depp .......................... 600/427 |
| 5,438,991 A | 8/1995 | Yu et al. |
| 5,471,546 A | 11/1995 | Nunan ......................... 385/11 |
| 5,537,452 A | 7/1996 | Sheopard et al. ............. 378/65 |

(Continued)

FOREIGN PATENT DOCUMENTS

DE 42 23 488 A1 1/1994

(Continued)

OTHER PUBLICATIONS

Balter, James M. et al., "Daily Targeting of Intrahepatic Tumors for Radiotherapy," Int. J. Radiation Oncology Biol. Phys., vol. 52, No. 1 (2002), pp. 266-271.

(Continued)

*Primary Examiner*—Courtney Thomas
(74) *Attorney, Agent, or Firm*—Blakely, Sokoloff, Taylor & Zafman LLP

(57) ABSTRACT

A radiation therapy treatment machine that has a stereoscopic imaging system, which includes a rotatable open gantry on which is placed a first diagnostic radiation source, a first diagnostic imager, and a therapeutic radiation source.

32 Claims, 9 Drawing Sheets

U.S. PATENT DOCUMENTS

| | | | |
|---|---|---|---|
| 5,692,507 | A | 12/1997 | Seppi et al. |
| 5,727,554 | A | 3/1998 | Kalend et al. ............... 600/587 |
| 5,751,781 | A | 5/1998 | Brown et al. ................. 378/65 |
| 5,823,192 | A | 10/1998 | Kalend et al. ............... 128/845 |
| 5,956,382 | A | 9/1999 | Wiener-Avnear et al. |
| 6,020,159 | A | 2/2000 | Black et al. ............... 435/69.1 |
| 6,031,888 | A | 2/2000 | Ivan et al. ..................... 378/20 |
| 6,041,097 | A | 3/2000 | Roos et al. |
| 6,104,778 | A | 8/2000 | Murad |
| 6,104,780 | A | 8/2000 | Hanover et al. ............... 378/92 |
| 6,138,302 | A | 10/2000 | Sashin et al. ................... 5/600 |
| 6,144,875 | A | 11/2000 | Schweikard et al. |
| 6,222,901 | B1 | 4/2001 | Meulenbrugge et al. |
| 6,266,393 | B1 | 7/2001 | Ein-Gal ....................... 378/152 |
| 6,307,914 | B1 | 10/2001 | Kunieda et al. ............... 378/65 |
| 6,325,537 | B1 | 12/2001 | Watanabe ................... 378/197 |
| 6,325,758 | B1 | 12/2001 | Carol et al. ................. 600/439 |
| 6,345,114 | B1 * | 2/2002 | Mackie et al. ............... 382/132 |
| 6,370,421 | B1 | 4/2002 | Williams et al. ............ 600/433 |
| 6,381,302 | B1 * | 4/2002 | Berestov ....................... 378/41 |
| 6,385,286 | B1 * | 5/2002 | Fitchard et al. ............... 378/65 |
| 6,385,288 | B1 | 5/2002 | Kanematsu ................... 378/65 |
| 6,429,578 | B1 | 8/2002 | Danielson et al. ... 313/105 CM |
| 6,459,769 | B1 | 10/2002 | Cosman ....................... 378/147 |
| 6,480,560 | B2 | 11/2002 | Hsieh ............................. 378/8 |
| 6,508,586 | B2 | 1/2003 | Oota ........................... 378/196 |
| 6,526,123 | B2 | 2/2003 | Ein-Gal ....................... 378/152 |
| 6,600,810 | B1 | 7/2003 | Hughes ....................... 378/152 |
| 6,621,889 | B1 | 9/2003 | Mostafavi ..................... 378/65 |
| 6,721,386 | B2 | 4/2004 | Bulkes et al. .................. 378/8 |
| 6,778,850 | B1 | 8/2004 | Adler et al. ................ 600/427 |
| 6,798,717 | B2 | 9/2004 | Wiener-Avnear et al. ... 367/180 |
| 6,842,502 | B2 | 1/2005 | Jaffray et al. ................. 378/65 |
| 6,865,248 | B1 | 3/2005 | Rasche et al. ................. 378/8 |
| 6,888,919 | B2 * | 5/2005 | Graf ............................ 378/65 |
| 6,914,959 | B2 * | 7/2005 | Bailey et al. ................. 378/65 |
| 6,937,696 | B1 | 8/2005 | Mostafavi ..................... 378/95 |
| 2001/0001807 | A1 | 5/2001 | Green ......................... 600/411 |
| 2001/0008271 | A1 | 7/2001 | Ikeda et al. |
| 2003/0007601 | A1 | 1/2003 | Jaffray et al. |
| 2004/0068169 | A1 | 4/2004 | Mansfield et al. .......... 600/407 |

FOREIGN PATENT DOCUMENTS

| | | |
|---|---|---|
| DE | 196 14 643 A1 | 10/1997 |
| EP | 0062941 B1 | 9/1984 |
| EP | 0205720 A1 | 12/1986 |
| EP | 0480035 B1 | 11/1994 |
| FR | 2 269 745 | 11/1975 |
| FR | 2 551 664 | 3/1985 |
| GB | 1 328 033 | 8/1973 |
| JP | HEI 5 1993-57028 | 3/1993 |
| WO | WO 85/03212 A1 | 8/1985 |

OTHER PUBLICATIONS

Swindell, William et al., "Computed Tomography With a Linear Accelerator With Radiotherapy Applications," Med. Phys., vol. 10, No. 4, Jul./Aug. 1983; pp. 416-420.

Mosleh-Shirazi, Mohammad Amin et al., "A Cone-Beam Megavoltage CT Scanner for Treatment Verification in Conformal Radiotherapy," Radiotherapy and Oncology, vol. 48 (1998), pp. 319-328.

Midgley, S. et al., "A Feasibility Study for Megavoltage Cone Beam CT Using A Commerical EPID," Phys. Med. Biol., vol. 43 (1998), pp. 155-169.

Ruchala, K.J. et al., "Megavoltage CT on a Tomotherapy System," Phys. Med. Biol., vol. 44 (1999), pp. 2597-2621.

Nakagawa, Keiichi, M.D. et al., "Megavoltage CT-Assisted Stereotactic Radiosurgery for Thoracic Tumors: Original Research in the Treatment of Thoracic Neoplasms," Int. J. Radiation Oncology Biol. Phys., vol. 48, No. 2, (2000), pp. 449-457.

Groh, B.A. et al., "A Performance Comparison of Flat-Panel Imager-Based MV and kV Conebeam CT," Med. Phys., vol. 29, No. 6, Jun. 2002, pp. 967-975.

Uematsu, Minoru et al., "Daily Positioning Accuracy of Frameless Stereotactic Radiation Therapy With a Fusion of Computed Tomography and Linear Accelerator (FOCAL) Unit: Evaluation of Z-Axis With a Z-Marker," Radiotherapy and Oncology, vol. 50, No. 3, Mar. 1999, pp. 337-339.

Uematsu, Minoru, M.D. et al., "A Dual Computed Tomography Linear Accelerator Unit for Stereotactic Radiation Therapy: A New Approach Without Cranially Fixated Stereotactic Frames," Int. J. Radiation Oncology Biol. Phys., vol. 35, No. 3 (1996), pp. 587-592.

Uematsu, Minoru, M.D. et al, "Intrafractional Tumor Position Stability During Computed Tomography (CT)-Guided Frameless Stereotactic Radiation Therapy for Lung or Liver Cancers With a Fusion of CT and Linear Accelerator (FOCAL) Unit," Int. J. Radiation Oncology Biol. Phys., vol. 48, No. 2 (2000), pp. 443-448.

Jaffray, David A., Ph.D. et al., "A Radiographic and Tomographic Imaging System Integrated Into a Medical Linear Accelerator for Localization of Bone and Soft-Tissue Targets," Int. J. Radiation Oncology Biol. Phys., vol. 45, No. 3 (1999), pp. 773-789.

Pisani, Laura, M.S. et al., "Setup Error in Radiotherapy: On-line Correction Using Electronic Kilovoltage and Megavoltage Radiographs," Int. J. Radiation Oncology Biol. Phys., vol. 47, No. 3 (2000), pp. 825-839.

Drake, D.G. et al, "Characterization of a Fluoroscopic Imaging System for kV and MV Radiography," Med. Phys., vol. 27, No. 5, May 2000, pp. 898-905.

Jaffray, D.A. and Siewerdsen, J.H., "Cone-Beam Computed Tomography with a Flat-Panel Imager: Initial Performance Characterization," Med. Phys., vol. 27, No. 6, Jun. 2000, 1311-1323.

Fahrig, R. and Holdsworth, D. W., "Three-Dimensional Computed Tomographic Reconstruction Using a C-Arm Mounted XRII: Image Based Correction of Gantry Motion Nonidealities," Med. Phys., vol. 27, No. 1, Jan. 2000, pp. 30-38.

Feldkamp, L.A. et al. "Practical Cone-Beam Algorithm," J. Opt. Soc. Am. A., vol. 1, No. 6, Jun. 1984; pp. 612-619.

Siewerdsen, Jeffery H. and Jaffray, David A., "Optimization of X-Ray Imaging Geometry (With Specific Application to Flat-Panel Cone-Beam Computed Tomography)," Med. Phys., vol. 27, No. 8, Aug. 2000, pp. 1903-1914.

Siewerdsen, Jeffery H. and Jaffray, David A., "Cone-Beam Computed Tomography With a Flat-Panel Imager: Magnitude and Effects of X-Ray Scatter," Med. Phys., vol. 28, No. 2, Feb. 2001, pp. 220-231.

Cho, Paul S. et al., "Cone-Beam CT for Radiotherapy Applications," Phys. Med. Biol., vol. 40 (1995), pp. 1863-1883.

PCT Search Report, International Application No. PCT/US03/22725, International filing date Jul. 22, 2003.

Jaffray, David A. et al., "Flat-Panel Cone-Beam Computed Tomography for Image-Guided Radiation Therapy", Int. J. Radiation Oncology Biol. Phys., vol. 53, No. 5 (2002), pp. 1337-1349.

Varian Medical Systems, Oncology Systems, Portal Vision, Image Guided Radiotherapy (1999) Brochure.

Ragan, "Correction for Distrotion in a Beam Outline Transfer Device in Radiotherapy CT-Based Simulation", Med. Phys. 20(1), Jan./Feb. 1993, pp. 179-185.

Kuhn, "AIM Project A2003: COmputer VIsion in RAdiology (COVIRA)", Computer Methods and Programs in Biomedicine, 1994, Citation from Dissertation Abstracts, 1 page.

Keys, A CCTV-Microcomputer Biostereometric System for Use in Radiation Therapy (Topography, Medical Physics, Tissue Compensators), 1984, Citation from Energy Science and Technology, 1 page.

Kutcher et al., "Three dimensional radiation treatment planning", Citation from Engineering Index, 1988, 2 pages.

Redpath, et al., "Use of a Simulator and Treatment Planning Computer as a CT Scanner for Radiotherapy Planning", 1984, Citation from INSPEC., 1 page.

Elliott, "Interactive Image Segmentation for Radiation Treatment Planning", IBM Systems Journal, 1992, Citation from Medline (R) Database, 1 page.

Kushima et al., "New Development of Integrated CT Simulation System for Radiation Therapy Planning", Kobs J Med Sci., 1993, Citation from Medline (R) Database, 1 page.

Gademann et al., "Three-Dimensional Radiation Planning. Studies on Clinical Integration", Strahlenther Onkol, 1993, 1 page.

Ragan, "Correction for Distortion in a Beam Outline Transfer Device in Radkotherapy CT-based Simulation", Med Phys., 1993, 1 page.

Andrew et al., "A Video-Based Patient Contour Acquisition System for the Design of Radiotherapy Compensators", Med Phys., 1989, 1 page.

Reynolds, "An Algorithm for Three-Dimensional Visualization of Radiation Therapy Beams", Med Phys., 1988, 1 page.

Mohan, "Intersection of Shaped Radiation Beams with Arbitrary Image Sections", Comput Methods Programs Biomed, 1987, 1 page.

Brewsterfuauf, "Automatic Generation of Beam Apertures", Medical Physics, 1993, 1 page.

Hara et al., "Radiotherapeutic System", 00480035/EP-B1, Citation from World Patent, 1994, 1 page.

Moore, "Radiation Image Generating System and Method", 1992020202/WO-A1, 1992, 1 page.

Seppi, "Computed Tomography Apparatus Using Image Intensifier Detector", 1992000567/WO-A1, 1 page.

Bova, "Dosimetric Technique for Stereotactic Radiosurgery", 1990014129/WO-A1, 1990, 1 page.

Kazufumi, "Radiation Treatment Device", 05057028 JP, 1993, 1 page.

Inamura, "CT Simulator For Radiotherapy", 63294839 JP, 1988, 1 page.

Moore, "Radiation Image Generating System and Method", Citation from US Patent, Issued 1993, 2 pages.

Nishihara, "Therapeutic Apparatus", Issued 1991, 2 pages.

Jaffray, "Cone-Beam CT: Application in Image Guided External Beam Radiotherapy and Brachytherapy", IEEE, 2000, 2 pages.

Ning et al., "An Image Intensifier-Based Volume Tomographic Angiography Imaging System: System Evaluation," SPIE, vol., . 2432, pp. 280-290.

"Advanced Workstation for Irregular Field Simulation and Image Matching", Copyright 1999, MDS Nordion, 7 pages.

Masahiro et al., "Patient Beam Positioning System Using CT Images", Phys. Med. Biol., 1982, vol. 27, No. 2, pp. 301-305, printed in Great Britain.

Fujita, K., "Three-Dimensional Conformal Set-Up of Prostate Cancer by Adjustment of Actual Clinical Target Volume (CTV) to Virtual CTV Using Three Fiducial Markers and Fluoroscopic Real-Time Tracking System," J. Radiat. Oncol. Biol. Phys., 2001; 51 (3S1): Abstract No. 2303, PMID: 16; 1 page.

Keall, P.J., et al., "Motion adaptive x-ray therapy: a feasibility study," Physics in Medicine and Biology, 46 (2001) pp. 1-10.

Kitamura, K., et al., "Migration of the Internal Fiducial Gold Marker Implanted into Prostate and Liver Treated with Real-Time Tumor-Tracking Radiation Treatment (RTRT)," I.J. Radiat. Oncol. Biol. Phys., 2000; 48 (3S1): Abstract No. 2161; 2 pp.

Kitamura, K., et al., "Three-Dimensional Intra-Fractional Movement of Prostate Measured During Real-Time Tumor-Tracking Radiotherapy in Supine and Prone Treatment Positions," Int. J. Radiat. Oncol. Biol. Phys., vol. 53, No. 5, 2002, pp. 1117-1123.

Lopresti, B.J., et al., "Implementaion and Performance of an Optical Motion Tracking System for High Resolution Brain PET Imaging," IEEE Transactions on Nuclear Science, vol. 46, No. 6, Dec. 1999; pp. 2059-2067.

Robb, R.A., "3-Dimensional Visualization in Medicine and Biology," Handbook of Medical Imaging: Processing and Analysis, ed. Isaac N. Bankman, Academic Press, San Diego, CA, Chapter 42, pp. 685-712, 2000.

Shimizu, S., et al., Fluoroscopic Real-Time Tumor-Tracking Radiation Treatment (RTRT) Can Reduce Internal Margin (IM) and Set-up Margin (SM) of Planning Target Volume (PTV) for Lung Tumors; I.J. Radiat. Oncol. Biol. Phys., 2000; 48 (3S1): Abstract No. 110; 2 pp.

Takai, et al., "Method and Apparatus for Irradiating a Target," U.S. Appl. No. 10/037,477, filed Jan. 2, 2002; 39 pp.

Keall, Paul, "4D IMRT: Imaging, Planning and Delivery," R01 Grant application CA 93626, Jan. 31, 2001, pp. 1-53.

* cited by examiner

GANTRY MOUNTED STEREOSCOPIC IMAGING SYSTEM

FIELD OF THE INVENTION

The present invention pertains in general to oncology radiation therapy. In particular, the invention involves an X-ray and electron radiotherapy machine used in radiation treatment applications.

BACKGROUND

The use of linear accelerators for the generation of a beam of either electrons or X-rays onto a target area or volume is well known. An electron gun can provide the source of electrons and after generating a stream of electrons, components in the radiotherapy machine can convert the electrons to X-rays. A flattening filter can flatten the X-ray beam, which can be further shaped to match target volume geometry with a multileaf collimator. A digital detector can be mounted and mechanically or electronically scanned synchronously with the mechanically or electronically scanned paraxial X-ray beam, providing continuous monitoring of alignment of the patient's anatomy. These systems typically provide either static fixed field radiation therapy or fully dynamic intensity modulated radiation therapy (IMRT) used by the medical community in the treatment of cancer. Advances in radiation delivery maintain the premise to maximize dose to the tumor while minimizing dose to the surrounding normal tissue. With emerging techniques to improve conformal radiotherapy, there is new emphasis on increased accuracy and reproducibility of target positioning.

Target positioning, i.e. the accurate positioning of the tumor in a radiation field, is one of the challenges inherent in radiotherapy treatment since the incorrect placement of the tumor in the radiation field is one of the most significant factors leading to the failure of local tumor-control radiation therapy. The main sources of the problem result from the fact that there is a natural motion of organs inside the body, which can range, for example, from approximately a millimeter in the case of the brain inside the skull, to several centimeters for the organs in the trunk above the diaphragm. Another factor relates to changes within an organ that can change its shape such as accepting, losing, or transferring fluids. In addition, changes to the organ can occur over the course of successful treatment, and as the tumor shrinks in volume, normal tissue, which had been displaced, returns to its original position within the volume under radiation treatment, i.e. the treatment volume.

An integrated approach is used to position the treatment volume, which consists of a gross positioning step, a coarse positioning step, and a fine positioning step. The gross positioning step can involve posture correction of the patient, while coarse positioning can locate the treatment volume relative to external body landmarks. The fine positioning step can locate the treatment volume with respect to internal landmarks, motion compensation, and gating of the treatment beam.

For example, U.S. Pat. No. 6,144,875, discusses a method of using both the coarse positioning and fine position treatment approaches to determine the position of an internal moving target region such as an internal organ, where external and internal markers (landmarks) may be used, and a model of their relative motions based on a series of images is determined prior to treatment. During treatment, little information is available on the placement of the internal landmarks except when the internal markers are periodically imaged using invasive devices, such as x-rays. Therefore, the position of external landmarks are used in real time during treatment by inferring the placement of the internal markers by referencing the pre-operative model of the relative motion of the internal and external markers. However, a problem occurs during the actual operation, namely, that it is difficult to obtain x-ray images more than once every predetermined number of seconds due to concerns about exposing the patient to too much radiation and due to the fact that the treatment beam cannot operate when x-ray imaging is being done. Here, the x-ray imaging alone would therefore be too slow to follow breathing motion with high precision without the use of external landmarks.

Traditionally, to accurately verify tumor location using the fine positioning approach, detectors such as X-ray film or electronic X-ray imaging systems are commonly used in the radiation treatment diagnostic process. In the case of electronic imaging, the megavolt therapeutic X-rays emerging from the patient can be used to generate images. However, these methods at target location deliver images of low contrast and insufficient quality. As a result, imaging with megavoltage radiation is used primarily for verification, that is, to confirm that the treatment volume is being radiated. These problems associated with utilizing high energy X-rays produced by a megavolt electron beam are the result of interacting with matter (for example, due to Compton scattering, in which the probability of interactions is proportional to the electron density).

Low energy X-rays typically have energies of about 125 peak kilovolts (kVp) or below, where a significant portion of the interactions with matter is photoelectric and the interactions are proportional to the cube of electron density. Low energy X-rays are more useful to provide accurate targeting or diagnostic information because tissue in the human body is typically of low density and as a result, the contrast achieved in low energy X-rays is far superior to that obtained with megavoltage X-rays. Therefore, distinctions of internal landmark features and the imaging of other features not perceptible with high energy X-rays are possible using kV energy. As a result, two separate imagers, each sensitive to an energy range, i.e. either the megavolt source or the kV source are used in treatment.

FIG. 1 is an illustration of a radiotherapy clinical treatment machine to provide therapeutic and diagnostic radiation, each directed to a different imager. One method taught is to have a radiotherapy machine with a therapeutic radiation source directed to a therapeutic imager along a first axis and a diagnostic X-ray source directed to a diagnostic imager along a second axis that is 90° from the first axis. This apparatus provides for the application of therapeutic radiation source capable of propagating radiation in the megavoltage (MV) energy range and for the use of kilovoltage (kV) diagnostic radiation to a separate imager. After generation of a diagnostic image by the diagnostic radiation source, the therapeutic X-ray source will rotate to the position of the diagnostic image and use the diagnostic image data for treatment of the treatment volume.

Another method taught is to incorporate a low energy X-ray source inside the treatment head of the accelerator capable of positioning itself to be as coincident with the high energy X-ray source as possible. With this approach, a high energy X-ray target is modified to include a compact 125 kV electron gun to be mounted to a moveable flange at the base of the high energy source with the cathode of the gun operably coupled to the upstream end of a drift tube. By engaging an actuator, the kV electron gun can provide radiation to a second imager that is sensitive to kV energy for providing target information. The diagnostic imager can be positioned opposite the kV electron gun with the treatment volume in between.

Therapeutic treatment can then be moved to the position used by the diagnostic imager. The therapeutic treatment beam as applied to the treatment volume can be shaped based on the data from the diagnostic imager.

SUMMARY

A method and apparatus is disclosed for generating two or more digital images of a treatment volume that can be taken from different positions. In addition, by merging any two such images, a stereoscopic representation may be formed of the treatment volume from which a radiation treatment dose can be shaped and directed to the treatment volume.

A radiotherapy clinical treatment machine, such as, for example, one capable of providing intensity modulated radiation therapy (IMRT), can include a rotatable gantry attached to a drive stand. One or more diagnostic radiation sources, each with opposing diagnostic imagers, can be attached to the gantry. A therapeutic (treatment) radiation source and a therapeutic imager (verification imager) can also be positioned on the gantry. Software algorithms in a computer can take data from the one or more diagnostic imagers, taken at two locations, and merge the data into a stereoscopic representation of the treatment volume. Using shape and distance data determined from the stereoscopic representation, the therapeutic radiation source can generate treatment radiation of a determined shape, duration, and intensity, i.e. a dose. After passing through a patient, the therapeutic radiation source can also provide radiation to the verification imager.

In one embodiment, two diagnostic radiations sources, each with an opposing diagnostic imager, can be positioned on the rotatable gantry. Also on the gantry, a therapeutic radiation source can be centered between the two diagnostic radiation sources. The diagnostic radiation sources can first radiate a treatment volume and then the two diagnostic imagers. Digital data from the two diagnostic imagers can be used real time and/or may be stored in a database. Using a computer, the digital data from the two diagnostic imagers can be merged into a stereoscopic representation of a volume existing within a patient that is to be treated, such as a tumor. The stereoscopic representation can be used to direct the therapeutic radiation source to the treatment volume. The gantry can then be rotated to a new position for generation of more digital images and further radiation treatment.

BRIEF DESCRIPTION OF THE DRAWINGS

The present invention is illustrated by way of example and not limitation in the figures of the accompanying drawings, in which like references indicate similar elements and in which.

DETAILED DESCRIPTION

Figure 1:
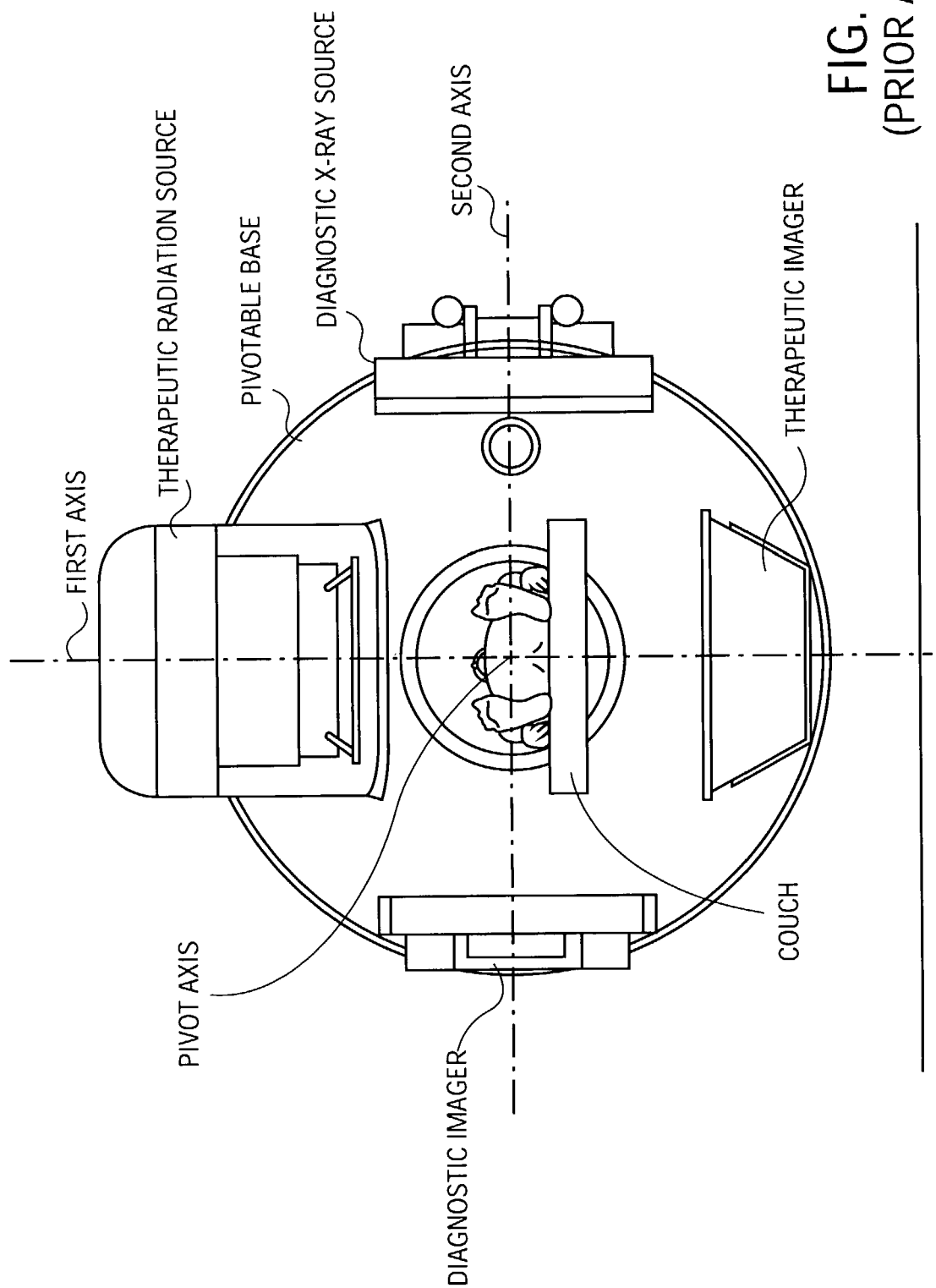
FIG. 1 is an illustration of a radiotherapy machine having a therapeutic radiation source and a diagnostic X-ray source directed to a diagnostic imager in the prior art.

In the following description, for purposes of explanation, numerous specific details are set forth in order to provide a thorough understanding of the present invention. It will be evident, however, to one skilled in the art that the present invention may be practiced without these specific details. In some instances, well-known structures and devices are shown in gross form rather than in detail in order to avoid obscuring the present invention. These embodiments are described in sufficient detail to enable those skilled in the art to practice the invention, and it is to be understood that other embodiments may be utilized and that logical, mechanical, electrical, and other changes may be made without departing from the scope of the present invention.

A method and apparatus for a radiotherapy clinical treatment machine, capable of providing a stereoscopic diagnostic representation from the perspective of any radial location in order to tailor doses of therapeutic radiation to be applied from that location, is disclosed. For purposes of discussing the invention, it is to be understood that various terms are used by those knowledgeable in the art to describe apparatus, techniques, and approaches.

Visualizable objects in medicine extend across a vast range of scale, from individual molecules and cells, through the varieties of tissue and interstitial interfaces, to complete organs, organ systems and body parts, and include functional attributes of these systems, such as biophysical, biomechanical and physiological properties. Visualization in three dimensions of such objects and their functions is now possible with the advent of high resolution tomographic scanners and imaging systems. Medical applications include accurate anatomy and function mapping, enhanced diagnosis, education and training and accurate treatment planning.

The higher MV range energy levels generated for treatment, i.e. therapeutic energy, can also radiate a digital therapeutic (verification) imager after passing through the patient volume. Such imaging can provide general treatment volume location information, i.e. verification that in general the treatment volume is being radiated correctly. However, digital diagnostic imagers, separate from the verification imager, can be necessary since low kV energy X-ray images are generally used in soft tissue diagnostics. The lower energy radiation, generated at two different angled positions, can provide current treatment volume position data from which to calculate each therapeutic dose with a high degree of accuracy.

Stereoscopic representations of a treatment volume can be obtained by merging digital data from one or more digital imagers taken at two locations. In one embodiment, the MV and kV radiation sources and imagers can be fixed on a rotatable gantry. Both MV and kV energy radiation sources and imagers can be approximately directed toward a center of rotation of the gantry. A treatment bench can position a patient, and therefore a treatment volume, within a radius of operation for both the treatment and the stereoscopy apparatus. At a single gantry position or through gantry rotation, multiple single images can be generated at different radial locations and any two images may be selected and merged by a computer into a stereoscopic representation of the treatment volume. The stereoscopic representation can be generated to provide 2-dimensional (2D) cross-sectional data for a selected radial position to apply therapeutic radiation, i.e. a perspective. The stereoscopic representation can be used to determine a distance from a tumor to be treated and the therapeutic radiation source. The stereoscopic representation of the treatment volume can be determined for any perspective that falls within an angle created by the locations where the two digital images were generated. With a cross-section outline, and a distance to the tumor, a therapeutic treatment beam can be accurately tailored to deliver a conformal dose to the tumor.

In one embodiment, data from two low energy (kV) radiation sources directed to two digital kV imagers can be merged to provide the stereoscopic representation data of the treatment volume, from which can be computed a dosimetry to be applied by a treatment beam that is centered within the two kV radiation sources. Alternatively, it should be appreciated that the individual image data and the stereoscopic representation data can be stored, i.e. in a computer database.

Any two stored images taken from different locations can be selected and merged by the computer for a determination of shape and distance for targeting the tumor from a location. A treatment beam thus directed can maximize a dose to the target volume and minimize a dose to critical structures in the treatment field, i.e. conformal therapy, where the beam profiles are shaped to deliver the cancer-killing dose to the irregular tumor volume while sparing healthy tissues near the treatment field.

Figure 2A:
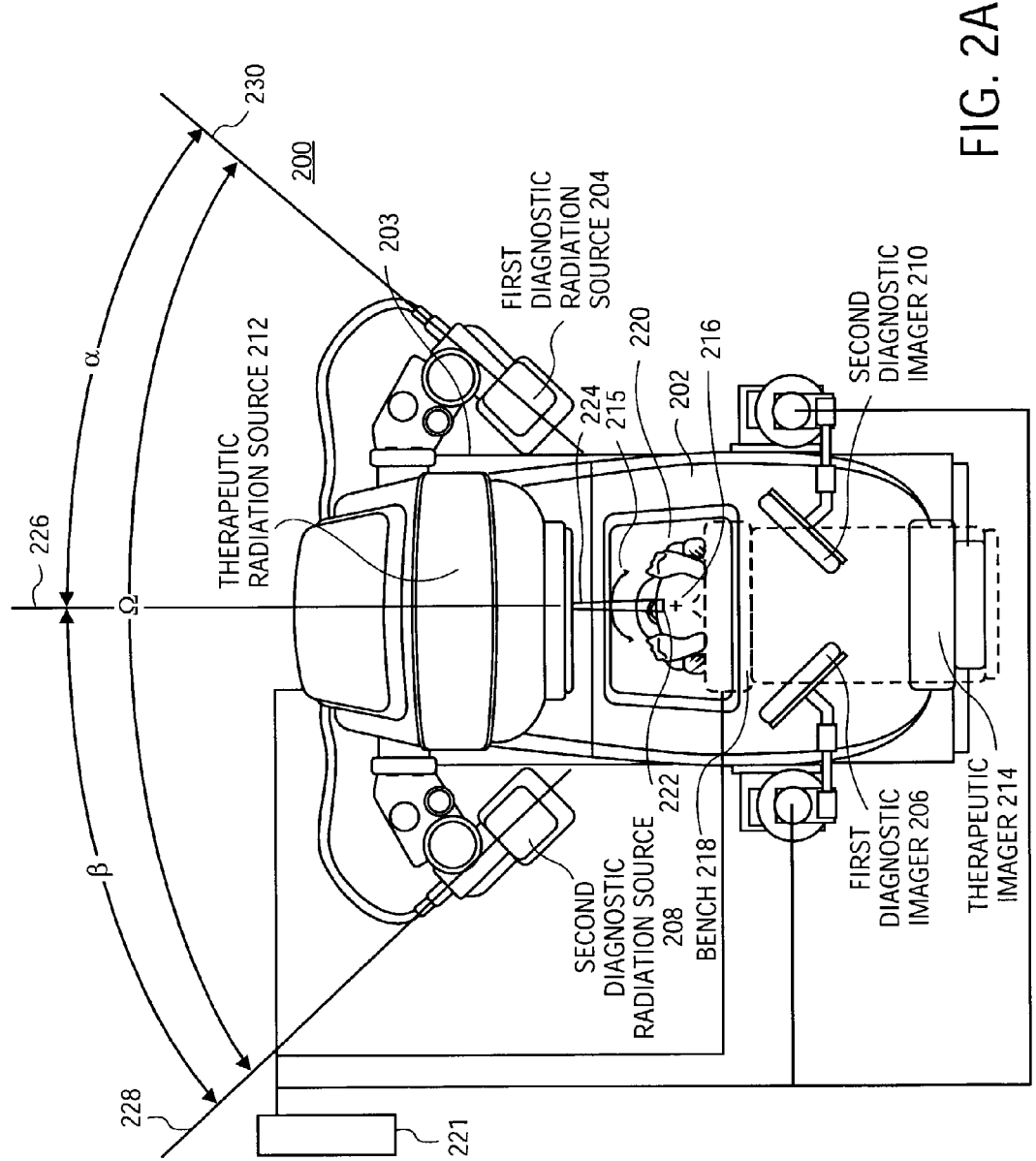
FIG. 2A is an illustration of one embodiment of a radiotherapy clinical treatment machine having a rotatable gantry and a stereoscopic diagnostic imaging system.
Figure 2B:
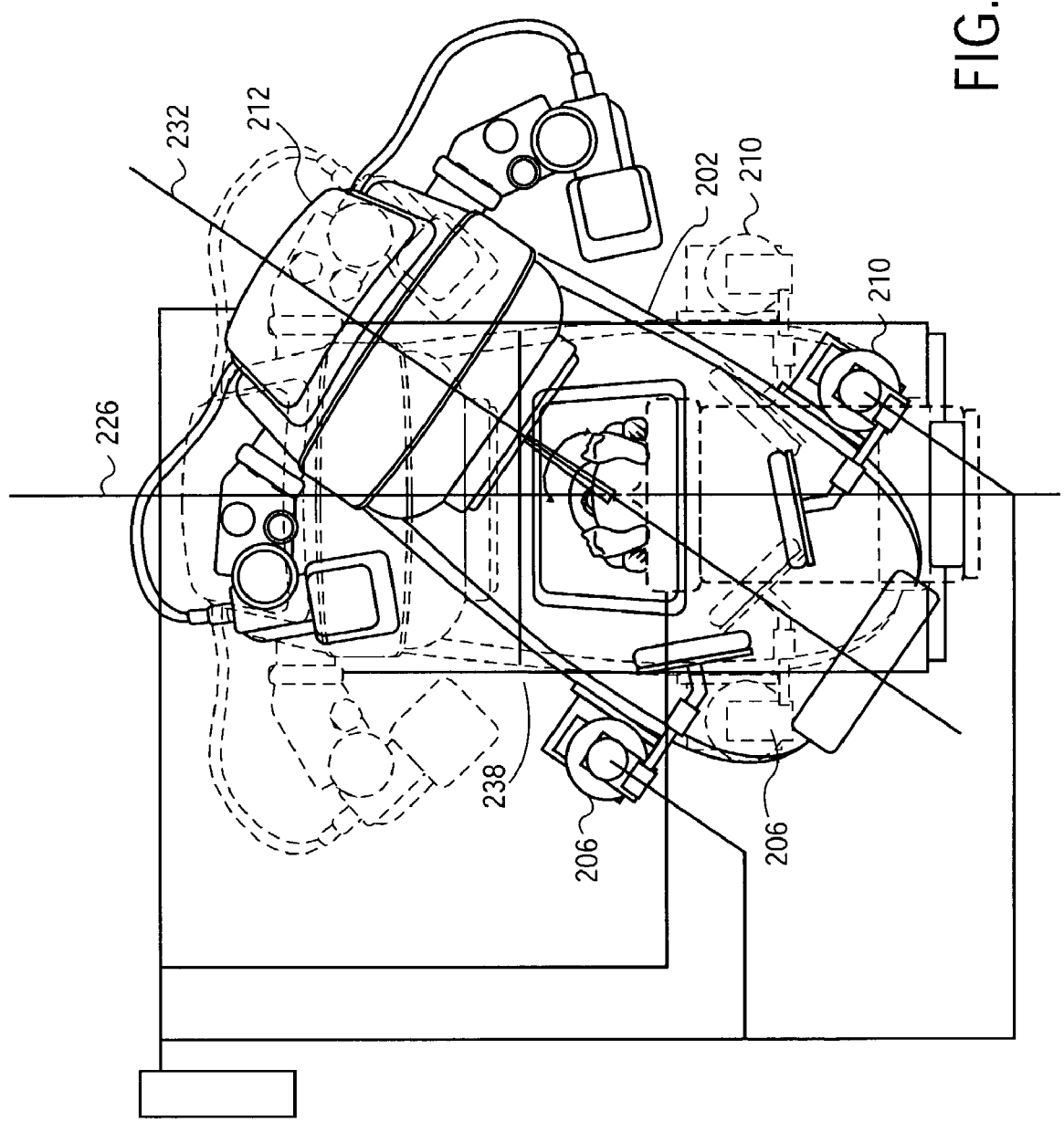
FIG. 2B is an illustration of the one embodiment where the gantry has rotated to a second position.

FIG. 2A is an illustration of one embodiment of a radiotherapy clinical treatment machine having a stereoscopic diagnostic imaging system positioned on a rotatable open gantry. FIG. 2B is an illustration of the radiotherapy clinical treatment machine rotated to a second position. The rotatable gantry 202 can be pivotably attached to a drive stand 203 of the radiotherapy clinical treatment machine 200. The gantry 202 can be capable of 360-degree rotation 215 about a centerline 216 such as, for example, to a first position (FIG. 2A) and a second position (FIG. 2B). A first diagnostic radiation source 204 opposing a first diagnostic imager 206, a second diagnostic radiation source 208 opposing a second diagnostic imager 210, and a therapeutic imager 214 facing a therapeutic radiation source 212, can be disposed on the rotatable gantry 202. It should be understood that this open gantry design provides a care provider full access to the patient. In this way, the care provider might better position the patient in an angle most beneficial to the treatment.

In one embodiment, the therapeutic radiation source 212 can be radially located between the two kV radiation sources 204 and 208. Each kV radiation source 204 and 208 can be offset from the therapeutic radiation source 212 by angles alpha ($\alpha$) and beta ($\beta$) respectively. The sum of angles $\alpha$ and $\beta$ can form angle gamma (Q) and gamma can be in the range of approximately 10–170 degrees. Each angle, $\alpha$ and $\beta$ can be in the range of 5–85 degrees such that angles $\alpha$ and $\beta$ may or may not be equal. In the one embodiment as shown in FIG. 2A, angles $\alpha$ and $\beta$ are each 45 degrees, i.e. the therapeutic radiation source 212 is centered within a 90 degree angle formed by the locations 228 and 230 of the two kV radiation sources 204 and 208. The radiation sources 204, 208, 212 and the imagers 206, 210, and 214 can be oriented to direct radiation or receive radiation respectively, to and from the treatment volume position 222, which can be approximately at the center of rotation of the gantry 202. A benefit of this embodiment is that the gantry can rotate the therapeutic radiation source to a first location previously determined for treatment. The kV imagers can generate the two images, the computer can merge the two images into the stereoscopic representation, and the therapeutic radiation source can radiate the treatment volume, all without rotating the gantry from the first location. This can reduce the time between stereoscopic generation and the application of the treatment beam which can reduce the time available for the treatment volume to move, such as, for example, through movement internal to the body or external such as through patient voluntary-involuntary motion.

A treatment bench 218 can be positioned adjacent to the gantry 202 to place the treatment volume within the range of operation for the radiation sources 204, 208 and 212 and the imagers 206, 210, and 214. The bench 218 can be capable of translating in multiple planes for positioning and re-positioning the patient 220 and therefore the treatment volume 222.

The gantry 202 can rotate 214 about the centerline 216 to place the radiation sources 204, 208 and 212 and kV imagers 206, 210, and 214 at any position 360 degrees around the treatment volume 222 from which to generate digital images and direct treatment radiation. Image data can be delivered to the computer 221 and where the computer 221 can merge the image data generated from two different radial locations into a stereoscopic representation of the treatment volume 222. The stereoscopic representation can be used by the targeting components (not shown) of the radiotherapy clinical treatment machine 200. The data representing each image can be stored by the computer 221.

The computer 221 can be linked to the radiation sources 204, 208, and 212, imagers 206, 210, and 214 and other translatable devices such as, for example, the treatment bench 218 and the rotatable gantry 202. Software in the computer can generate each stereoscopic representation from digital information provided by the kV imagers 206 and 210. Following a pre-determined treatment plan and the stereoscopic data, radiation of the treatment volume 222 from selected radial locations can occur. Control software in the computer 221 can be used to operate the radiotherapy clinical treatment machine 200, such as, for example, to rotate and translate the above devices 202, 204, 206, 208, 210, 212, 214, and 218 to position the target volume 222 in line with the treatment beam 224 that is shaped to the target volume 222.

The stereoscopic information can generate a distance and a 2-dimensional (2D) cross-section shape of the treatment volume 222 for applying a correspondingly shaped treatment beam 224. The 2D shape can be generated by the computer to correspond to the treatment volume cross-section facing the therapeutic treatment beam at the radial location selected for treatment. 2D shape information can direct a multileaf collimator (not shown) or a dynamically multileaved collimator (also not shown) that is capable of shaping the therapeutic beam 224 emanating from the therapeutic radiation source 212. After passing through the treatment volume 222, therapeutic radiation can contact the therapeutic (verification) imager 214. Information from the therapeutic imager 214 can confirm (verify) during application of the treatment beam 224 that the treatment volume 222 is being properly targeted.

Figure 3A:
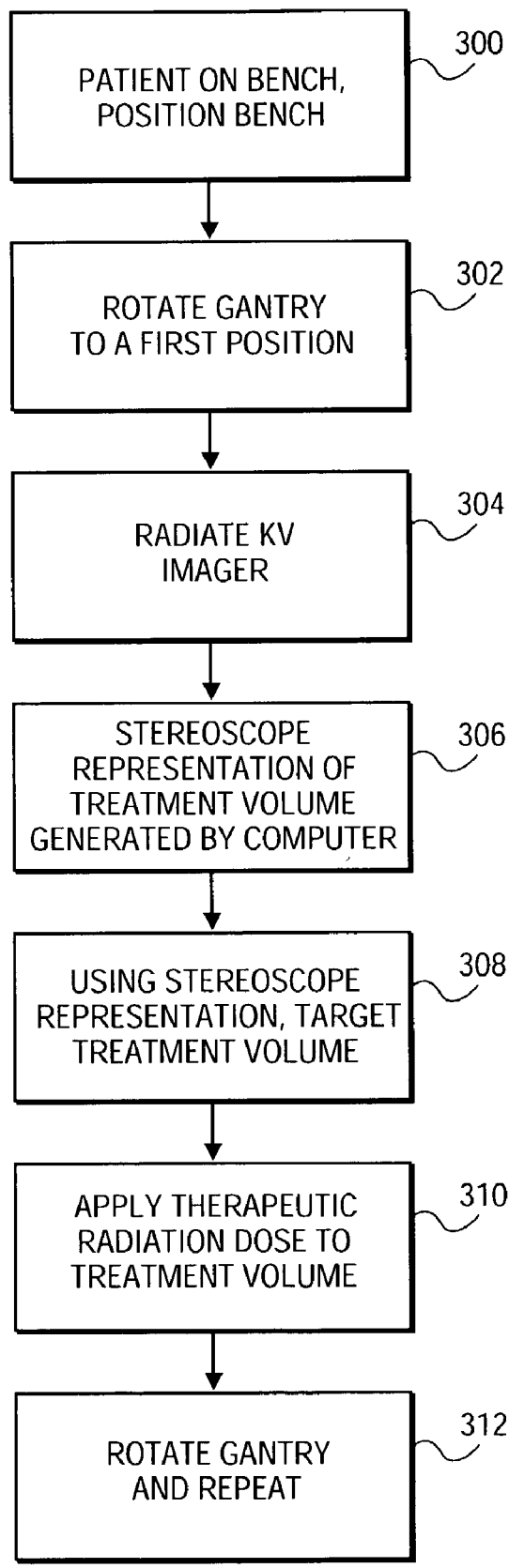
FIG. 3A is a flow diagram of one embodiment of a method of use of the stereoscopic diagnostic imaging system.

FIG. 3A is a flow diagram of one embodiment of a method for using the radiotherapy clinical treatment machine. After development of the treatment plan, a patient can be placed on a treatment bench and the bench positioned relative to the radiotherapy clinical treatment machine as shown in FIGS. 2A & 2B (operation 300). The gantry can rotate to a first position as shown in FIG. 2A (operation 302). From the first position, radiation from a first kV radiation source can impinge a first kV imager and radiation from a second kV radiation source can impinge a second kV imager (operation 304). Data from the two kV imagers can be merged by the computer into a stereoscopic representation of a treatment volume using a computer (operation 306). Next, using data from this stereoscopic representation, a therapeutic radiation source can target the treatment volume where the gantry is still located at the first position (operation 308). A radiation dose, tailored to the treatment volume from the first gantry position can be applied (operation 310). To continue the treatment, the gantry can now rotate to a next position, such as, for example, the second position, and repeat the process to radiate the treatment volume (operation 312).

Figure 3B:
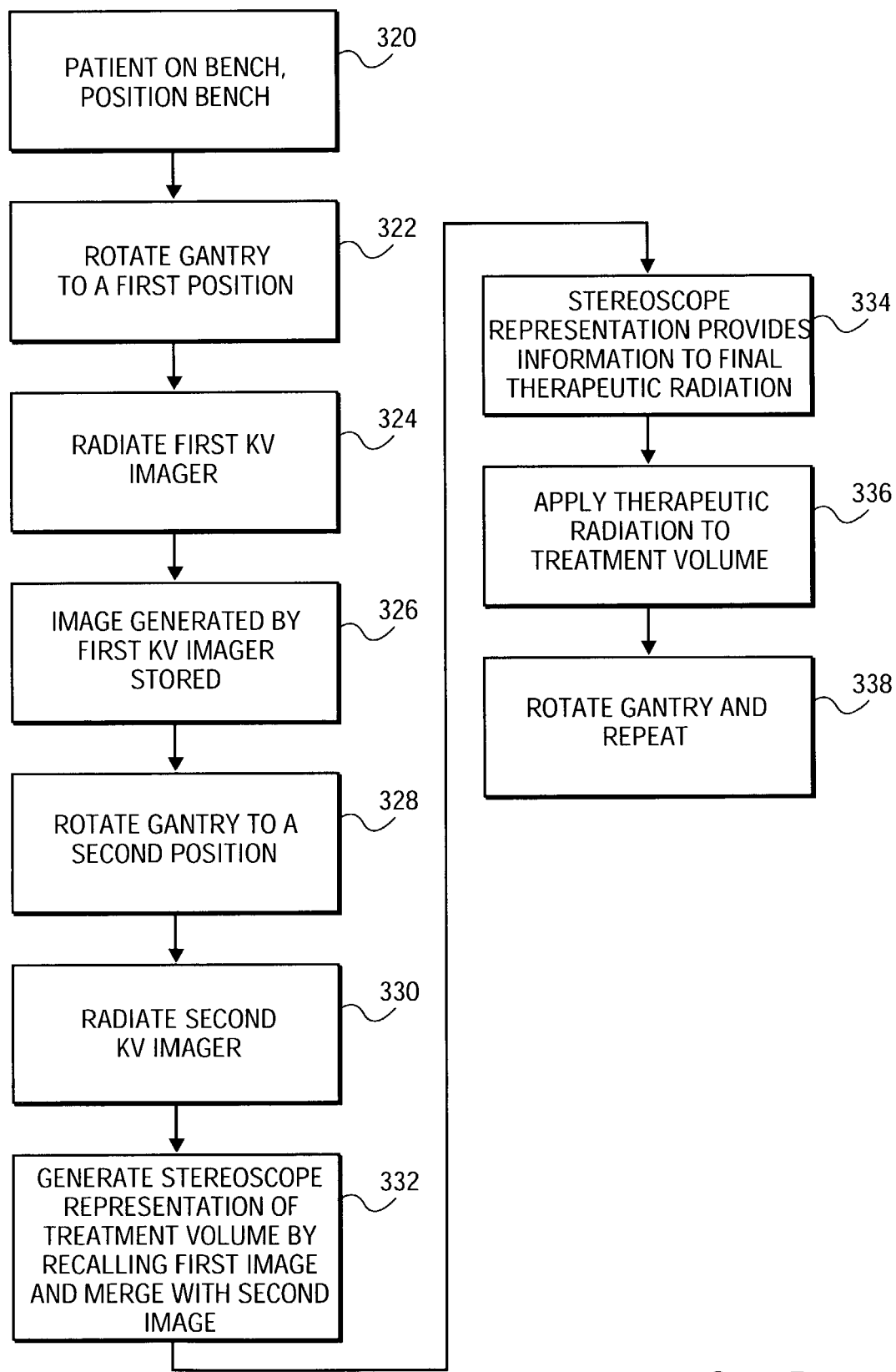
FIG. 3B is a flow diagram of an alternate embodiment of a method of use of the stereoscopic diagnostic imaging system.

FIG. 3B is a flow diagram of an alternate embodiment of a method for using the radiotherapy clinical treatment machine. In this alternate embodiment using the radiotherapy clinical treatment machine as shown in FIGS. 2A & 2B, the computer can generate a stereoscopic representation of the treatment volume by selecting at least one stored digital image previously generated from a different gantry position. In the alternate embodiment the patient can be placed on the treatment bench (operation 320). The gantry can rotate to the first gantry position 226, as shown in FIG. 2A (operation 322). The first diagnostic radiation source can radiate the first diagnostic imager at the first gantry position (operation 324). A first image can be generated by the first diagnostic imager and stored in the computer (operation 326). The gantry can then rotate to a second position 232, as shown in FIG. 2B (operation 328). The second diagnostic radiation source can radiate the second diagnostic imager to generate a second image (operation 330). The computer can then generate a stereoscopic representation by recalling the first image and merging it with the second image being generated by the second imager (operation 332). From the second gantry position, the stereoscopic representation can be used to provide targeting information about the treatment volume (operation 334). After application of a radiation dose from the second gantry position, to the treatment volume (operation 336), the gantry can be again rotated and the process continued (operation 338).

The methods described above can select from any presently generated image/images or any previously generated image/images that have been stored, to merge for constructing the stereoscopic representation. A gantry position can be selected for application of the therapeutic radiation, such as, for example, by following the previously developed treatment plan. The two images selected, i.e. either from images currently being generated or from images stored in the database of the computer, can be taken at radial locations that are separated by less than 180 degrees. Using the two selected images, computer software can develop the stereoscopic representation that is in-line with the location from which therapeutic radiation is to be applied. Therefore, it is not necessary for the therapeutic radiation to be applied from a position that is physically centered between the two locations where the diagnostic radiation sources were placed (to generate the individual diagnostic images) since computer software can provide virtual stereoscopic representations for any desired radial location in-between the images.

For the most accurate treatment plans to succeed, very precise targeting of the tumor should be accomplished. Movement of the organ that includes the tumor can result from respiration of the patient, fluid transfers within the organ under treatment, and other small body adjustments made by the patient. Many cancers are not visible with conventional transmission x-ray imaging and as such, some type of marking system may be required to determine fine positioning of the tumor. Fiducial markers may be small pieces of metal embedded in tissues around the tumor or in the tumor tissues and also sometimes in bony structures. Since such markers are visible with transmission x-ray as well as more sophisticated imaging modalities such as for example CT imaging, they can be used as sign posts for locating the tumor surfaces to a high degree of accuracy.

Fine positioning of the tumor must be ongoing during the treatment and such updates can come from such markers and where the initial placement of the location of such markers relative to other known features can be confirmed with other imaging techniques. Such internal markers, or seeds, can provide a constant monitor of tumor position through the stereoscopic diagnostic images (and thus the stereoscopic images) that can have an accuracy for tumor targeting that is within the sub-millimeter level.

The radiation therapy machine can generate an electron beam, generally in the 4 to 25 megavolt (MV) energy range, to provide therapeutic electrons or X-rays to the volume on or within a patient that is undergoing treatment, i.e. a treatment volume. The single therapeutic imager can receive the therapeutic radiation after it has passed through the patient and treatment bench. The therapeutic imager, receiving the MV energy, can display coarse imaging information that can be sufficient to provide verification that the therapeutic beam is in-line with the tumor and that the exposed cross-sectional area of the treatment volume is being radiated properly.

The stereoscopic imaging system can have the two diagnostic imagers to each receive X-rays in the 50–150 kV range, typically 80–120 kV for providing diagnostic information on the shape and location of the treatment volume on or within the patient. Diagnostic imaging with kV energy can provide the targeting information necessary to align the therapeutic radiation beam to the treatment volume with a great deal of accuracy and to make a determination of the distance from the therapeutic beam head and the treatment volume "shape" (2D cross-section) relative to that position for shaping the treatment beam by a multileaf collimator and for determining radiation intensity.

Beam shaping, along with intensity modulation, can be accomplished by directing a therapeutic beam through a dynamic multileaf collimator. The multileaf collimator can include a series of stacked metal shims having a center of shim pairs where each shim of the pairs can be individually moved to create a shaped opening capable of shaping the therapeutic beam. To be effective, the radiation field should be large enough to radiate as much of the tumor as possible while at the same time minimize radiating healthy tissue. The collimator can be dynamic in that the shims can rapidly move to reshape the beam, which results in blocking the therapeutic beam from striking certain areas of the treatment volume. Such dynamic shaping can result in different areas of the tumor receiving different amounts of radiation over the time that a radiation dose is applied.

Figure 4A:
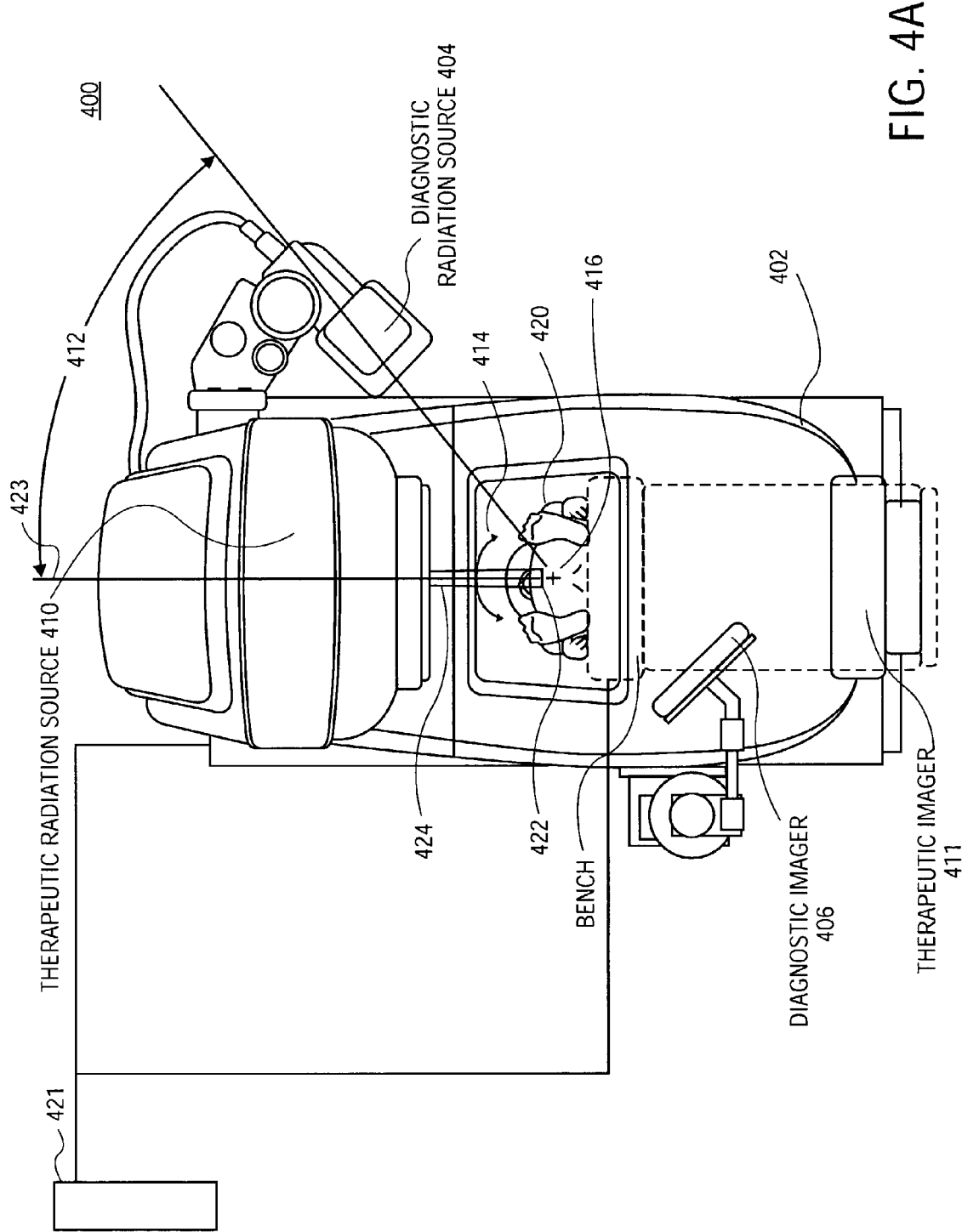
FIG. 4A is an illustration of an alternate embodiment of the rotatable gantry at a first position having a stereoscopic imaging system with a single diagnostic imager.
Figure 4B:
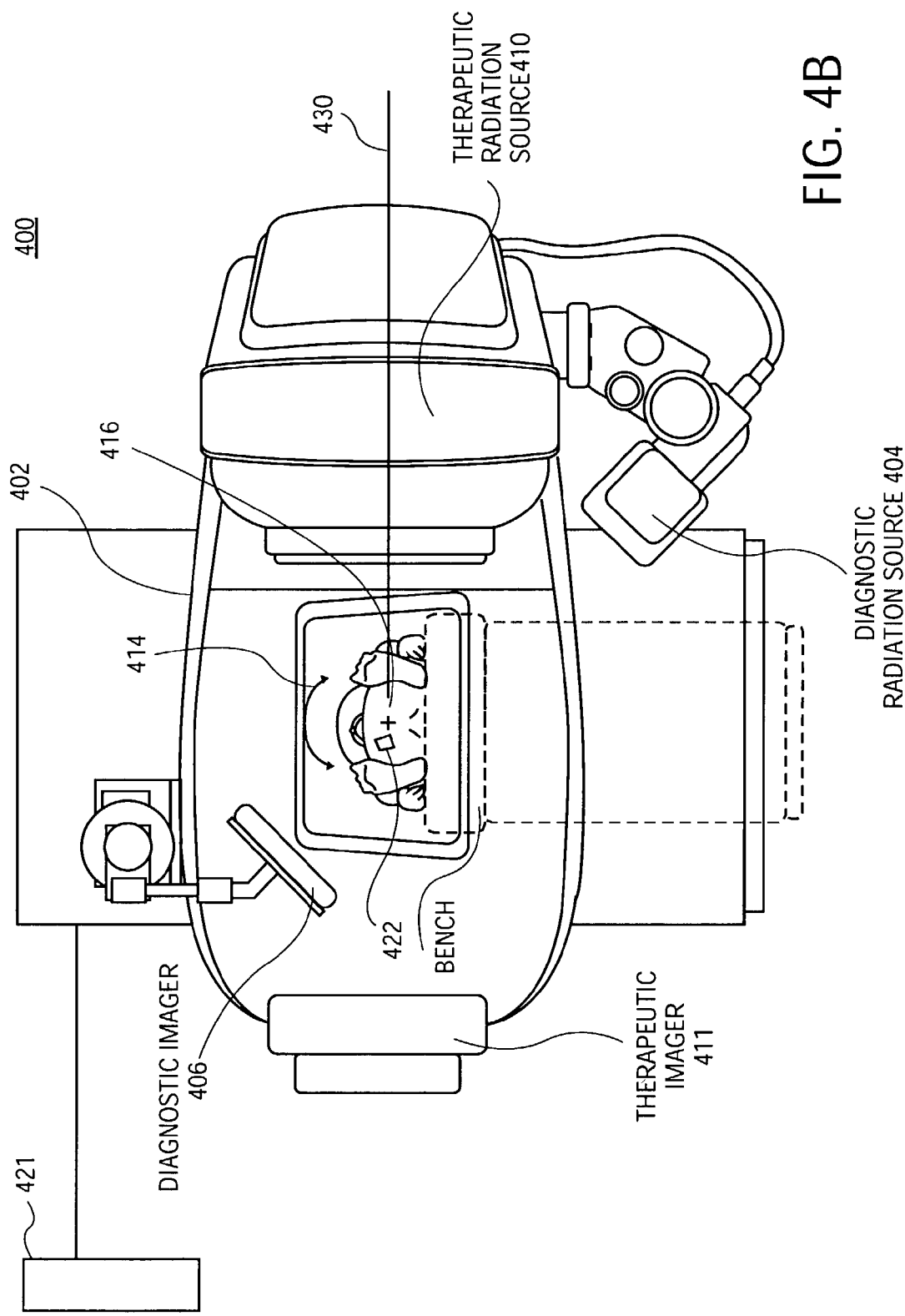
FIG. 4B is an illustration of the alternate embodiment showing rotation of the gantry to a second position.
Figure 4C:
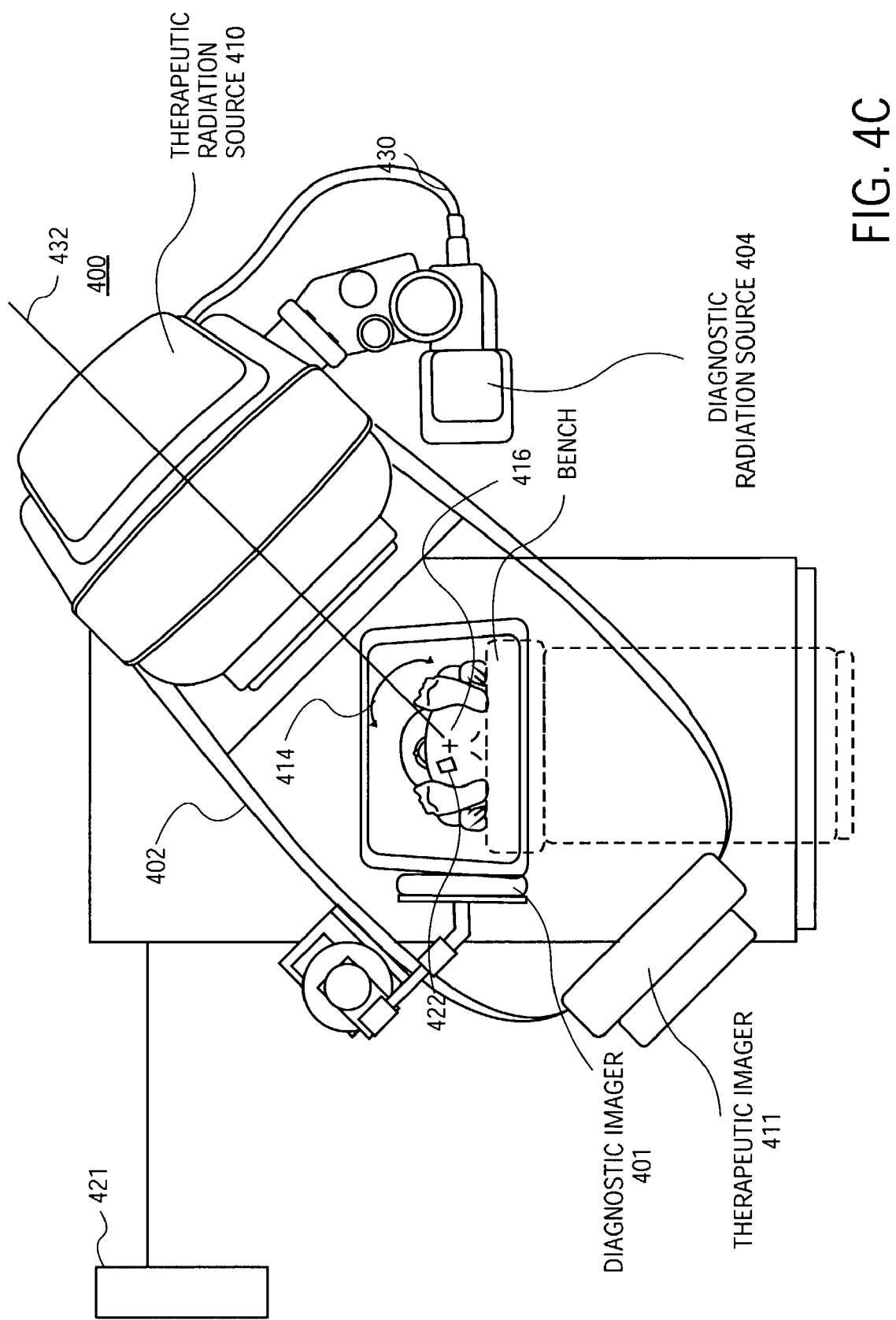
FIG. 4C is an illustration of the alternate embodiment showing rotation of the gantry to a third position.

FIGS. 4A, 4B & 4C are illustrations of an alternate embodiment of a radiation treatment machine providing stereoscopic imaging. FIG. 4A illustrates the radiation treatment machine generating a first image at a first position.

FIG. 4B is an illustration of the radiation treatment machine generating a second image at a second position. FIG. 4C illustration the radiation treatment machine delivering a therapeutic dose at a third position. The radiation therapy machine 400 can have a rotatable gantry 402. Positioned on the gantry 402 can be a therapeutic radiation source 410 with an opposing verification imager 411 and a diagnostic (kV) radiation source 404 with a diagnostic (kV) imager 406, all on the gantry 402. The kV radiation source 404 can be located at an angle 412 on the gantry 402, such as, for example 45 degrees from the position of the therapeutic radiation source 410. The gantry 402 can rotate (414) 360 degrees to place the radiation sources 404 and 410 at any position around a patient 420 and therefore a treatment volume 422. Image data can be delivered to the computer 421 and where the computer 421 can merge the image data generated from the different radial locations into a stereoscopic representation of the treatment volume 422. The computer 421 can also store the data representing each image.

FIG. 5A is a flow diagram of one embodiment of a method of use of MV and kV imaging to providing a stereoscopic representation. A treatment plan can be developed and after which, a patient can be placed on a treatment bench and the bench positioned relative to the radiotherapy clinical treatment machine (operation 500). The gantry can rotate to a first position as shown in FIG. 4A (operation 502). From the first position, a lower amount of radiation than used for a therapeutic dose can be applied from the MV radiation source to pass through the treatment volume to impinge a verification imager and create a first image (operation 504). First image data generated by the verification imager can be stored in a computer (operation 506). The gantry can rotate to a second position 430 as shown in FIG. 4B (operation 508). The kV radiation source can pass through the treatment volume to impinge the kV imager to form a second image (operation 510). Second image data from the kV imager can be stored in the database (operation 512). The gantry can move to a third position 432 as shown in FIG. 4C that is radially in-between the first and second gantry positions (operation 514). The computer can merge the two images into a stereoscopic representation of the treatment volume that is centered about the therapeutic radiation source position at the third gantry location 432 (operation 516). Although it should be understood that the third position need not be radially in-between the first and second gantry position to merge the two images into a stereoscopic representation. Next, using data from this stereoscopic representation, the therapeutic radiation source can target the treatment volume. Such targeting can include the computer system re-aligning the therapeutic radiation source and/or the patient to a corrected position for treatment. The stereoscopic representation data can also be used to correct a final treatment position and angle (operation 518). A radiation dose, tailored to the treatment volume from the third position 432 can be applied (operation 520). Following the treatment plan, the gantry can now rotate to a next position, such as, for example, a fourth position (not shown), and repeat the process to radiate the treatment volume (operation 522).

Prior to application of each therapeutic treatment beam, the treatment bench can be translated to align the treatment volume to the treatment beam. The combination of kV and MV beams to generate stereoscopic imaging does not provide image quality as good as purely kV generated images but if tracking a fiducial marker it can be distinctive enough to pick up and be used for the targeting process.

Figure 5:
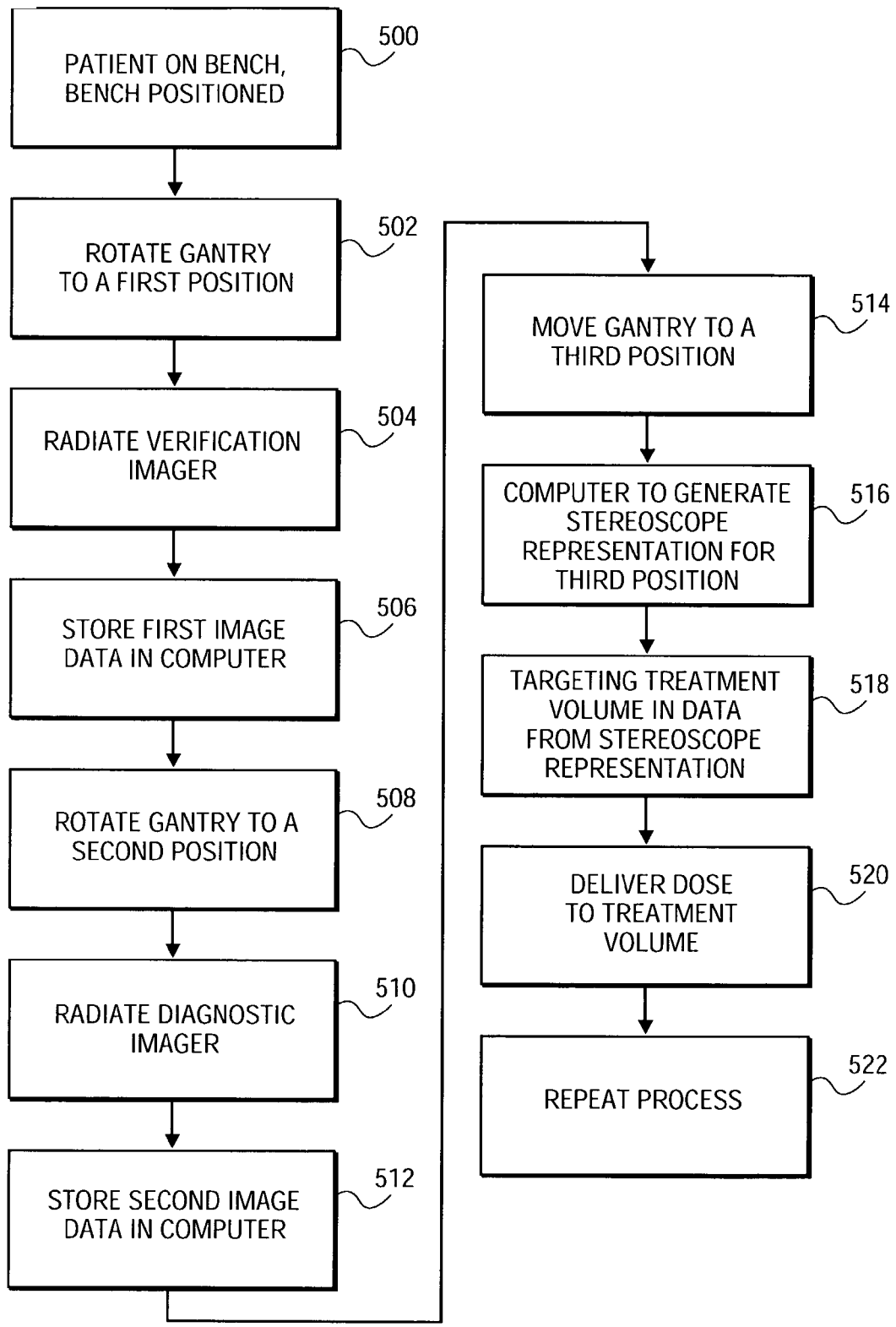
FIG. 5 is a flow diagram of another alternate embodiment of a method for using the stereoscopic imaging system.

It should be appreciated that that more or fewer processes may be incorporated into the method(s) illustrated in FIGS. 3A, 3B, and 5 without departing from the scope of the invention and that no particular order is implied by the arrangement of blocks shown and described herein. It further will be appreciated that the method(s) described in conjunction with FIGS. 3A, 3B, and 5 may be embodied in machine-executable instructions, e.g. software. The instructions can be used to cause a general-purpose or special-purpose processor that is programmed with the instructions to perform the operations described. Alternatively, the operations might be performed by specific hardware components that contain hardwired logic for performing the operations, or by any combination of programmed computer components and custom hardware components. The methods may be provided as a computer program product that may include a machine-readable medium having stored thereon instructions which may be used to program a computer (or other electronic devices) to perform the methods. For the purposes of this specification, the terms "machine-readable medium" shall be taken to include any medium that is capable of storing or encoding a sequence of instructions for execution by the machine and that cause the machine to perform any one of the methodologies of the present invention. The term "machine-readable medium" shall accordingly be taken to included, but not be limited to, solid-state memories, optical and magnetic disks, and carrier wave signals. Furthermore, it is common in the art to speak of software, in one form or another (e.g., program, procedure, process, application, module, logic . . . ), as taking an action or causing a result. Such expressions are merely a shorthand way of saying that execution of the software by a computer causes the processor of the computer to perform an action or produce a result.

It should be understood that the imagers, as described above, may be flat-panel imagers, such as, flat-panel amorphous silicon (a-Si) portal imaging devices, as well as other imaging devices that are well known to those of ordinary skill in the art.

Thus a method and apparatus for a stereographic imaging system on a radiation therapy clinical treatment machine having either a single or a dual kV imager to provide a stereoscopic representation of a treatment volume for therapeutic radiation targeting has been described. Any combination of stored digital images and actively generated images can be used to generate the stereoscopic representation. Further, using images taken no more than approximately 180 degrees apart from each other, a stereoscopic representation can be generated by a computer for any radial location within these two locations for applying the therapeutic radiation. Although the present invention has been described with reference to specific exemplary embodiments, it will be evident that various modifications and changes may be made to these embodiments without departing from the broader scope of the invention as set forth in the claims. Accordingly, the specification and drawings are to be regarded in an illustrative rather than a restrictive sense.

What is claimed is:

1. A radiation therapy treatment apparatus, comprising:
   a rotatable gantry on which is disposed:
      a first diagnostic radiation source protruding from a first location of the gantry;
      a first diagnostic imager protruding from the gantry; and
      a structure comprising a therapeutic radiation source protruding from a second location of the gantry, the first diagnostic radiation source and the therapeutic radiation source being different;

wherein the gantry rotates about an axis, and wherein the first diagnostic imager, and the structure comprising the therapeutic radiation source protrude from a plane perpendicular to the axis, and the first diagnostic radiation source is offset from a line extending through the therapeutic radiation source and the axis.

2. The apparatus of claim 1, further comprising a second diagnostic radiation source and a second diagnostic imager disposed on the rotatable gantry, the first diagnostic radiation source protruding from the plane, the second diagnostic radiation source protruding from the plane, and the second diagnostic imager protruding from the plane.

3. The apparatus of claim 2, wherein the first diagnostic radiation source and the second diagnostic radiation source are disposed at opposite sides of the therapeutic radiation source.

4. The apparatus of claim 3, wherein the first diagnostic radiation source and the second diagnostic radiation source are disposed approximately 45 degrees from the therapeutic radiation source.

5. The apparatus of claim 2, wherein the gantry is rotatable around a center line, the first diagnostic radiation source and first diagnostic imager are at a first set of opposing locations of the gantry, and the second diagnostic radiation source and second diagnostic imager are at a second set of opposing locations of the gantry;
further comprising a verification imager disposed on the rotatable gantry at a location opposing a location of the therapeutic radiation source of the gantry.

6. The apparatus of claim 1, further comprising a verification imager disposed on the rotatable gantry.

7. The apparatus of claim 1, further comprising a translatable patient bench.

8. The apparatus of claim 7, wherein the translatable patient bench to move in three planes.

9. The apparatus of claim 1, wherein the apparatus is an intensity modulated radiation therapy treatment machine.

10. The apparatus of claim 1, wherein the rotatable gantry is pivotably attached to a drive stand to provide 360 degree rotation.

11. The apparatus of claim 1, further comprises a computer system to generate a stereoscopic representation of a treatment volume from image data.

12. The apparatus of claim 11, wherein the stereoscopic representation to provide location information about the treatment volume to a multileaf collimator.

13. The apparatus of claim 1, wherein the first diagnostic imager is a flat-panel imager.

14. The apparatus of claim 1, wherein the gantry provides access by a care provider to a patient located along a center line of the gantry's rotation.

15. An intensity modulated radiation therapy machine, comprising:
a rotatable gantry on which is disposed:
means for generating a stereoscopic representation of a treatment volume from image data coupled to a computer system; and
a therapeutic radiation source comprising a structure including a multileaf collimator coupled to the computer system
wherein the gantry rotates about an axis, and wherein a first diagnostic imager and the structure comprising the therapeutic radiation source protrude from a plane perpendicular to the axis, and the first diagnostic imager is offset from a line extending through the therapeutic radiation source and the axis.

16. The apparatus of claim 15, further comprising:
means for positioning the treatment volume relative to a therapeutic radiation source disposed on the rotatable gantry based on the stereoscopic representation of the treatment volume.

17. A method for operating a radiation therapy treatment machine, comprising:
positioning a rotatable gantry to a radial position with respect to a center line of the gantry's rotation;
generating a first image of a treatment volume with a first kilovoltage (kV) radiation source and a first kV imager, the first kV radiation source disposed at a first location on the gantry;
generating a second image of the treatment volume with a second kV radiation source and a second kV imager, the second kV radiation source disposed at a second location on the gantry;
generating by computer, a stereoscopic representation of the treatment volume from a perspective of a third location on the gantry based on the first image and the second image;
targeting the treatment volume with data from the stereoscopic representation; and
applying a therapeutic radiation dose from the third location to the treatment volume.

18. The method of claim 17, wherein the therapeutic radiation dose is tailored by modifying parameters chosen from the group consisting of a time the therapeutic radiation is applied, a beam shape striking the treatment volume, a modulation of the beam shape, and an intensity of the therapeutic radiation.

19. The method of claim 17, wherein the imagers are flat-panel imagers.

20. The method of claim 17, further comprising repositioning the gantry to a different radial position with respect to the center line prior to applying the therapeutic radiation.

21. The method of claim 17, wherein the treatment volume is disposed within a patient, and further comprising a care provider accessing the patient after targeting and prior to applying.

22. A method for operating a radiation therapy treatment machine, comprising:
selecting a first image of a treatment volume from a first position;
selecting a second image of the treatment volume from a second position;
generating a stereoscopic representation of the treatment volume based on the first image and the second image; and
targeting the treatment volume from a third position with data from the stereoscopic representation,
wherein the first image is produced using a first radiation source and the second image is produced using a second radiation source disposed on the radiation therapy machine, wherein said first and said second radiation sources are angularly offset from each other.

23. The method of claim 22, further comprising:
applying therapeutic radiation to the targeted treatment volume from the third position.

24. The method of claim 22, further comprising generating the first image using a first kilovoltage radiation source and a first kilovoltage imager.

25. The method of claim 24, further comprising generating the second image using a second kilovoltage radiation source and a second kilovoltage imager.

26. The method of claim 24, further comprising generating the second image using a therapeutic radiation source and a verification imager.

27. The method of claim 22, further comprising:
generating the stereoscopic representation from a perspective of a third position; and
applying therapeutic radiation to the treatment volume based on the stereoscopic representation of the perspective of the third position.

28. The method of claim 22, further comprising using a computer to adjust a therapeutic radiation source position and a treatment bench to target the treatment volume with a therapeutic treatment beam.

29. The method of claim 22, wherein the generating the first image further comprises:
rotating a rotatable gantry to the first position and storing the first image in a computer.

30. The method of claim 22, wherein the generating the second image further comprises:
rotating a rotatable gantry to the second position and storing the second image in a computer.

31. The method of claim 24, further comprising generating the second image using the first kilovoltage radiation source and the first kilovoltage imager.

32. The method of claim 22 wherein the first and second images are a stored image and a generated image.

* * * * *